(12) United States Patent
Tanahashi

(10) Patent No.: US 10,534,169 B2
(45) Date of Patent: Jan. 14, 2020

(54) SWITCH UNIT, IMAGE PICKUP APPARATUS FOR ENDOSCOPE INCLUDING SWITCH UNIT, AND ENDOSCOPE INCLUDING SWITCH UNIT

(71) Applicant: OLYMPUS CORPORATION, Tokyo (JP)

(72) Inventor: Fuminori Tanahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/048,454

(22) Filed: Jul. 30, 2018

(65) Prior Publication Data

US 2018/0348502 A1 Dec. 6, 2018

Related U.S. Application Data

(63) Continuation of application No. PCT/JP2016/082324, filed on Oct. 31, 2016.

(30) Foreign Application Priority Data

Feb. 2, 2016 (JP) .................................. 2016-018118

(51) Int. Cl.
*G02B 23/24* (2006.01)
*A61B 1/00* (2006.01)
(Continued)

(52) U.S. Cl.
CPC ...... *G02B 23/2484* (2013.01); *A61B 1/00039* (2013.01); *A61B 1/00066* (2013.01);
(Continued)

(58) Field of Classification Search
CPC ............ G02B 23/2484; A61B 1/00039; A61B 1/00066; H01H 13/14
(Continued)

(56) References Cited

U.S. PATENT DOCUMENTS

2006/0100485 A1  5/2006 Arai et al.
2014/0275781 A1* 9/2014 Deng .................... A61B 1/0011
                                                    600/109
2016/0365203 A1* 12/2016 Hidai ..................... H01H 13/14

FOREIGN PATENT DOCUMENTS

JP        53-133704     *  3/1977 ............. H01H 13/14
JP        S53-133704 U    3/1977
(Continued)

OTHER PUBLICATIONS

International Search Report dated Dec. 27, 2016 issued in PCT/JP2016/082324.

*Primary Examiner* — Edwin A. Leon
*Assistant Examiner* — Iman Malakooti
(74) *Attorney, Agent, or Firm* — Scully, Scott, Murphy & Presser, P.C.

(57) ABSTRACT

A switch unit includes a frame body which is fixed to an opening section and in which a plurality of holes are formed, a plurality of switches provided in each of two of the plurality of holes, a soft switch cover that is disposed in each of the two holes and covers the plurality of switches, a first catch section formed as part of the switch cover in a position between the plurality of switches, a switch fixing member that is disposed in each of the two holes, is covered with the switch cover, fixes the plurality of switches to the opening section, and catches the first catch section in a position facing the first catch section, and a second catch section formed at an outer circumference of the switch cover and caught by the frame body.

10 Claims, 17 Drawing Sheets

(51) Int. Cl.
*A61B 1/04* (2006.01)
*A61B 1/05* (2006.01)

(52) U.S. Cl.
CPC ...... *A61B 1/00096* (2013.01); *A61B 1/00121* (2013.01); *A61B 1/00163* (2013.01); *A61B 1/00195* (2013.01); *A61B 1/042* (2013.01); *A61B 1/05* (2013.01); *G02B 23/2453* (2013.01); *A61B 1/00009* (2013.01); *A61B 1/00105* (2013.01); *G02B 23/2492* (2013.01)

(58) Field of Classification Search
USPC .............................. 200/51.04, 5 A, 318, 338
See application file for complete search history.

(56) References Cited

FOREIGN PATENT DOCUMENTS

| | | | | |
|---|---|---|---|---|
| JP | S59-029082 | U | 2/1984 | |
| JP | H02-164330 | A | 6/1990 | |
| JP | H04-169015 | A | 6/1992 | |
| JP | H08-112243 | A | 5/1996 | |
| JP | 2000-182459 | A | 6/2000 | |
| JP | 2000182459 | * | 6/2000 | ........... H01H 25/041 |
| JP | 2002-170453 | A | 6/2002 | |
| JP | 2004-267342 | A | 9/2004 | |
| JP | 2004-337188 | A | 12/2004 | |
| JP | 2013-056003 | A | 3/2013 | |

\* cited by examiner

SWITCH UNIT, IMAGE PICKUP APPARATUS FOR ENDOSCOPE INCLUDING SWITCH UNIT, AND ENDOSCOPE INCLUDING SWITCH UNIT

CROSS REFERENCE TO RELATED APPLICATION

This application is a continuation application of PCT/JP2016/082324 filed on Oct. 31, 2016 and claims benefit of Japanese Application No. 2016-018118 filed in Japan on Feb. 2, 2016, the entire contents of which are incorporated herein by this reference.

BACKGROUND OF THE INVENTION

1. Field of the Invention

The present invention relates to a switch unit that watertightly maintains the interior of a switch cover watertightly fixed to an opening section of an outer surface of an exterior member, an image pickup apparatus for endoscope including the switch unit, and an endoscope including the switch unit.

2. Description of the Related Art

As an example of an apparatus including a switch unit that watertightly maintains the interior of the switch unit, there is a known image pickup apparatus for endoscope.

An image pickup apparatus for endoscope picks up an image of a portion under inspection in a subject and outputs the picked-up image of the portion under inspection to a monitor, and, for example, there is a known configuration that allows the image pickup apparatus to be connected to an eyepiece portion (hereinafter referred to as eyepiece) provided at a proximal end of an insertion portion of the endoscope. An image pickup apparatus for endoscope, after used, needs to be reliably cleaned, disinfected, and sterilized. As a method for sterilizing an image pickup apparatus for endoscope, there is a known high-temperature, high-pressure steam sterilizing process of performing sterilization using high-temperature, high-pressure steam (hereinafter referred to as autoclave process).

In general, an internal unit including an image pickup unit formed of an image pickup device and an objective optical system, and other components in an image pickup apparatus for endoscope, is provided in an exterior member of the image pickup apparatus for endoscope. In the autoclave process, the high-temperature, high-pressure steam also enters the exterior member.

In the situation described above, when the high-temperature, high-pressure steam comes into contact with the image pickup unit, the image pickup device fails to normally operate and the objective optical system is fogged. It is therefore necessary to dispose the image pickup unit at a location in the exterior member where the high-temperature, high-pressure steam does not reach.

Japanese Patent Application Laid-Open Publication No. 2013-56003 discloses an image pickup apparatus for endoscope attached to the eyepiece portion of an endoscope. In the disclosed image pickup apparatus, an airtight enclosure made of a metal, such as, stainless steel is provided in an exterior member, and an internal unit is encapsulated in the airtight enclosure. According to the configuration, the airtight enclosure can protect an image pickup unit in the internal unit from high-temperature, high-pressure steam having entered the exterior member.

Japanese Patent Application Laid-Open Publication No. 2013-56003 further discloses a configuration in which a switch unit is watertightly provided in the exterior member of the image pickup apparatus for endoscope. Examples of the switch unit may include a focus adjusting button configured to move part of lenses provided in an image pickup unit in the internal unit forward or rearward for focus adjustment, a zoom button configured to move part of the lenses forward or rearward for adjustment of focus/magnification, a brightness adjusting button, a color adjusting button, and a release button.

The buttons are each so configured that a switch that forms the button is fit into an opening section provided in the exterior member on a switch basis and the switch is fixed to a switch fixing member provided in the opening section on a switch basis. Further, switch covers that cover the respective switches are watertightly fixed to the respective opening sections, whereby part of each of the switches is exposed through an outer surface of the exterior member to allow an operator to press the switch.

In the image pickup apparatus for endoscope disclosed in Japanese Patent Application Laid-Open Publication No. 2013-56003, a proximal point button and a distal point button, which are each the focus adjusting button, are provided independently of each other. Further, a Wide button and a Tele button, which are each the zoom button, are provided independently of each other.

There is also a known configuration in which the proximal point button and the distal point button are integrated with each other to form a single focus adjusting button and the Wide button and the Tele button are integrated with each other to form a single zoom button are both a known configuration. The configuration allows reduction in the number of buttons and the operator to readily recognize a desired button.

Specifically, in the case of the focus adjusting button, for example, the following configuration is known: the proximal point switch and the distal point switch are fit into a single opening section in the exterior member and fixed to a single switch fixing member provided in the opening section, and a single switch cover that covers both the proximal point switch and the distal point switch is watertightly fixed to the single opening section.

The configuration described above also applies to the zoom button.

When the autoclave process described above is carried out on the image pickup apparatus for endoscope, the pressure in the switch cover changes to negative or positive pressure with respect to atmospheric pressure.

SUMMARY OF THE INVENTION

A switch unit according to an aspect of the present invention includes a frame body which is fixed to an opening section and in which a plurality of holes are formed, a plurality of switches provided in each of two of the plurality of holes, a soft switch cover that is disposed in each of the two holes and covers the plurality of switches, a first catch section formed as part of the switch cover in a position between the plurality of switches, a switch fixing member that is disposed in each of the two holes, is covered with the switch cover, fixes the plurality of switches to the opening section, and catches the first catch section in a position facing the first catch section, and a second catch section formed at an outer circumference of the switch cover and caught by the frame body.

An image pickup apparatus for endoscope including a switch unit according to another aspect of the present invention includes the switch unit described above.

An endoscope including a switch unit according to another aspect of the present invention includes the switch unit described above.

DETAILED DESCRIPTION OF THE PREFERRED EMBODIMENT

An embodiment of the present invention will be described below in detail with reference to drawings. The drawings are diagrammatically drawn, and note that the relationship between the thickness and the width of each member, the ratio among thicknesses of the members, and other factors differ from actual values, and that some of the dimensional relationships and ratios, of course, differ among the drawings.

Figure 1:
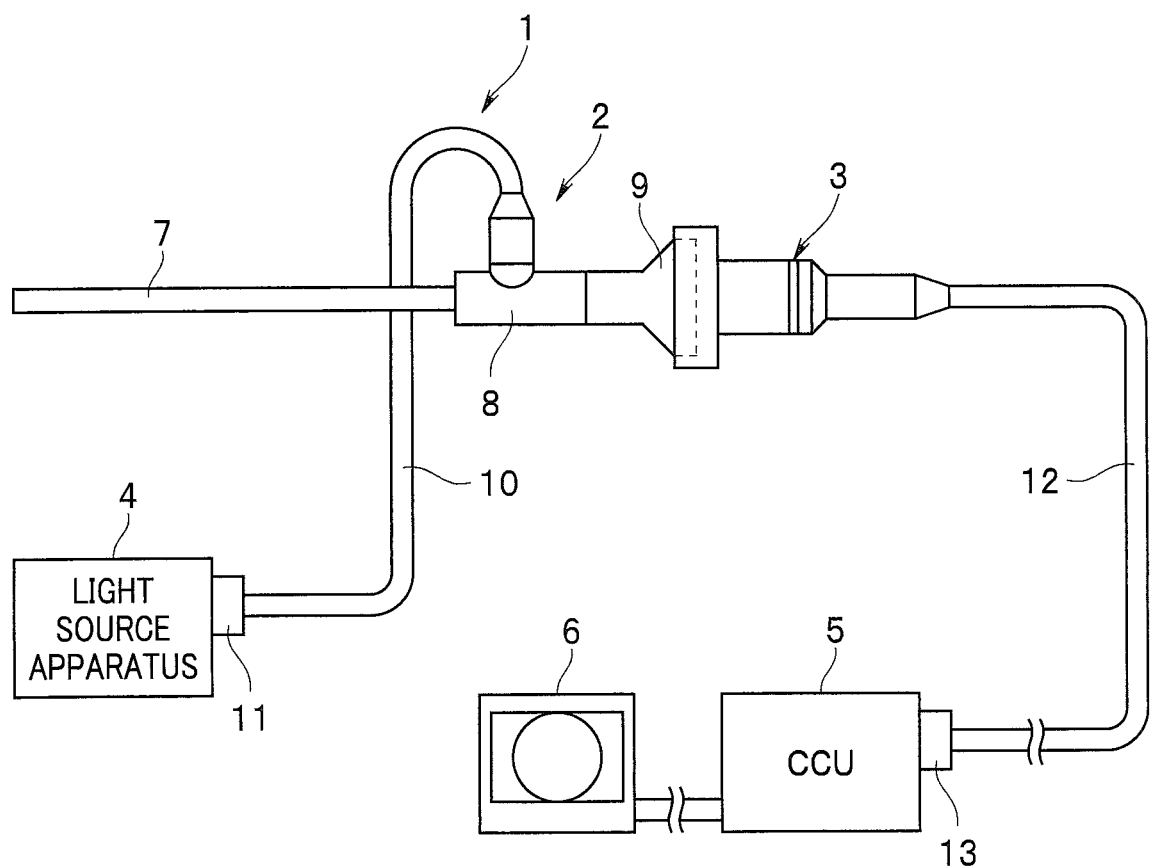
FIG. 1 shows an overview of the configuration of an endoscope system including an image pickup apparatus for endoscope including a switch unit according to an embodiment of the present invention.

FIG. 1 shows an overview of the configuration of an endoscope system including an image pickup apparatus for endoscope including a switch unit according to the present embodiment.

An endoscope system 1 includes an endoscope 2, a camera head 3, which includes a switch unit 270 (see FIG. 2), which is an image pickup apparatus for endoscope connectable to the endoscope 2 and will be described later, and a light source apparatus 4, which supplies the endoscope 2 with illumination light, as shown in FIG. 1.

The endoscope system 1 further includes a camera control unit (CCU) 5, which performs signal processing and other types of processing on an image pickup signal from the camera head 3, and a monitor 6, which displays a video signal outputted from the CCU 5.

The endoscope 2 is primarily formed of an elongated insertion section 7, a grasping section 8, which is provided at the proximal end of the insertion section 7 and thicker than the insertion section 7, and an eyepiece 9, which is provided at a proximal end of the grasping section 8.

A lightguide cable 10 is so provided that one end of the lightguide cable 10 is detachably attached via a connector 11 to the light source apparatus 4 and the other end of the lightguide cable 10 is connectable to a pipe sleeve provided at a side portion of the grasping section 8 of the endoscope 2.

The light emitted from a lamp that is not shown but is provided in the light source apparatus 4 is therefore supplied to the endoscope 2 via the lightguide cable 10 and radiated into a subject via an illumination window that is not shown but is provided at a distal end of the insertion section 7.

An optical image of the interior of the subject illuminated with the illumination light is formed by an objective optical system that is not shown but is provided at the distal end of the insertion section 7. The thus formed optical image is incident on a lens provided in the eyepiece 9 via a relay lens and other components that are not shown but are provided in the insertion section 7. An operator can therefore observe the optical image via the eyepiece 9.

The camera head 3 is connectable to the eyepiece 9 of the endoscope 2, as described above.

A camera cable 12 extends from the camera head 3, and an extended end of the camera cable 12 is detachably attached to the CCU 5 via a connector 13, which is provided at the extended end.

The CCU 5 produces an image signal based on the image pickup signal transmitted from the camera head 3 via the camera cable 12 and causes the monitor 6 to display the image of the interior of the subject as an endoscope image.

A specific configuration of the camera head 3 described above will next be described with reference to FIGS. 2 to 4.

Figure 2:
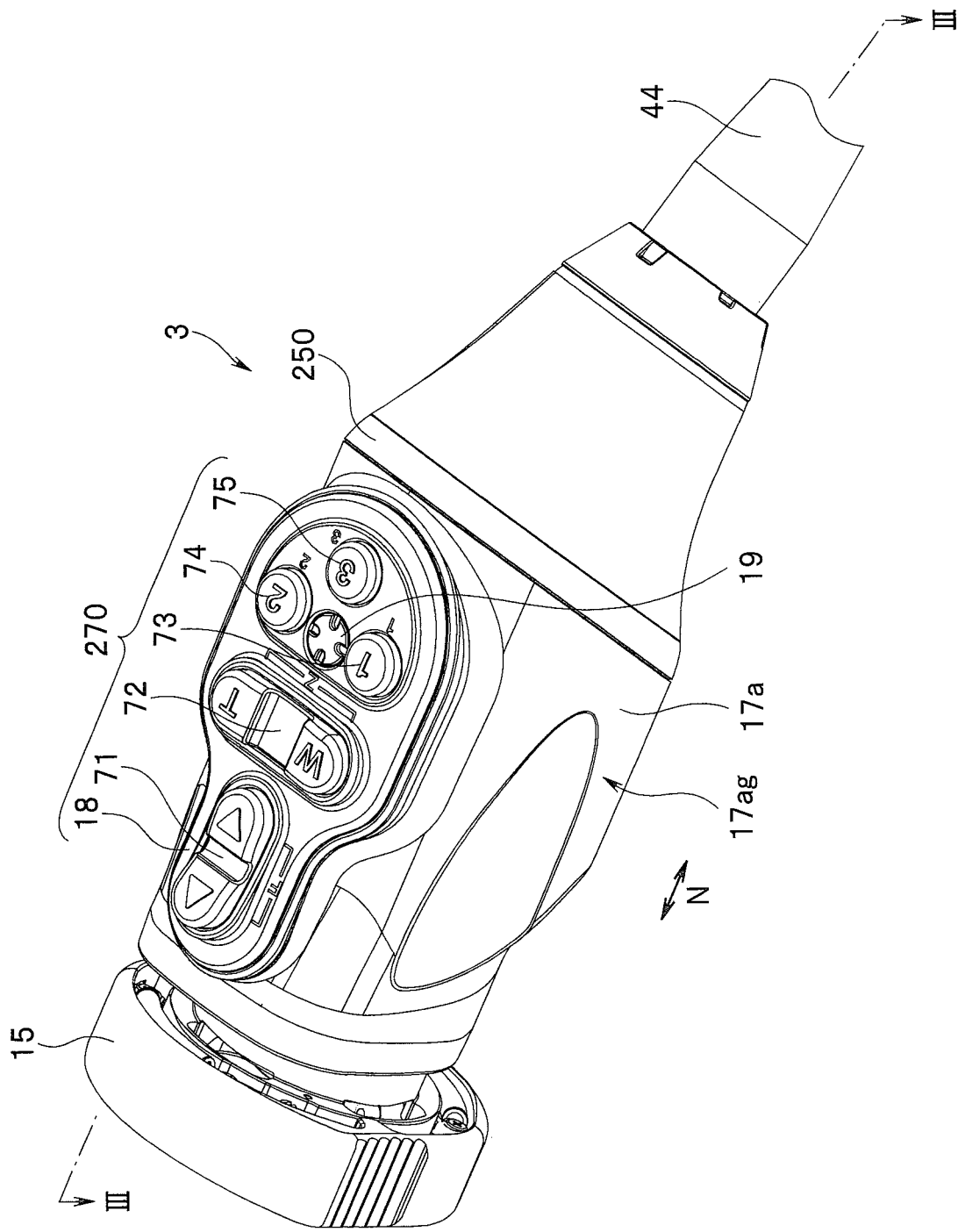
FIG. 2 is a perspective view showing a camera head in FIG. 1.

FIG. 2 is a perspective view of the camera head in FIG. 1. FIG. 3 is a partial cross-sectional view of the camera head taken along a line in FIG. 2. FIG. 4 is an enlarged partial cross-sectional view of a portion enclosed with a line IV in the camera head in FIG. 3.

Figure 3:
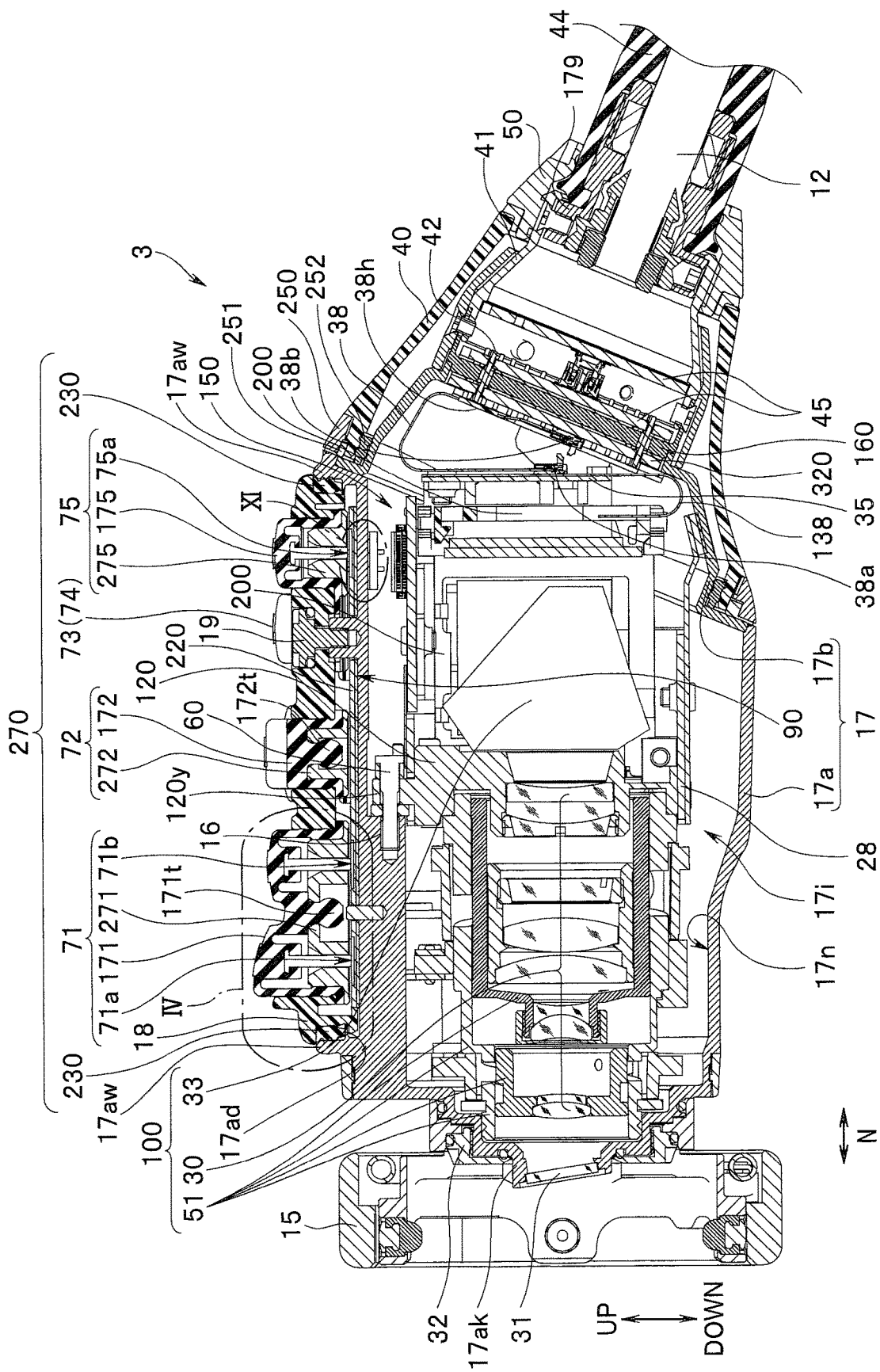
FIG. 3 is a partial cross-sectional view of the camera head taken along a line III-III in FIG. 2.

The camera head 3 is primarily formed of a coupler section 15 and an exterior member 17, a distal end of which is fixed to the coupler section 15, as shown in FIGS. 2 and 3.

The coupler section 15 is a member to which the eyepiece 9 of the endoscope 2 is connected, and the coupler section 15 is fixed to an outer circumference of a distal end 17ak of the exterior member 17 by using a fixing screw 32, as shown in FIG. 3.

The exterior member 17 is formed of a single layer made of a metal and airtightly maintains the interior of the exterior member 17 and includes a main cover 17a and a rear cover 17b, which is watertightly and airtightly fixed to a proximal end of the main cover 17a with solder, welding, or any other means. That is, the exterior member 17 also serves as an airtight enclosure.

The metal of which the exterior member 17 is formed may, for example, be titanium to achieve weight reduction. Further, the metal of which the exterior member 17 is formed is desirably a lightweight metal having low thermal conductivity.

The exterior member 17 may, however, be made of any metal that allows airtight welding performed to prevent entry of the high-temperature, high-pressure steam into an interior 17i in the autoclave process described above, such as stainless steel.

The switch unit 270, which is used to perform operation of picking up an image of the interior of the subject, is fixed along a longitudinal direction N of the camera head 3 to a side surface of an outer surface 17ag of the main cover 17a, specifically, the outer surface 17ag of an upper portion shown in FIG. 2. A detailed configuration of the switch unit 270 will be described later.

An internal unit 150 including an image pickup unit 100 is provided in the interior 17i, which is airtightly sealed by the exterior member 17, as shown in FIG. 3.

The image pickup unit 100 is primarily formed of a plurality of lenses 30, lens frames 51, which hold the lenses 30, an image pickup device 33, and electric parts, such as a variety of substrates.

More specifically, the plurality of lenses 30 are so positioned as to face along the longitudinal direction N to an observation window 31, which is airtightly fixed to the distal end 17ak of the main cover 17a with solder or any other material attached on a metalized outer circumference of the observation window 31, as shown in FIG. 3.

The observation window 31 is so positioned as to face the lenses in the eyepiece 9 in the longitudinal direction N when the eyepiece 9 of the endoscope 2 is connected to the coupler section 15 of the camera head 3.

In the interior 17i of the exterior member 17, the plurality of lenses 30 held by the lens frames 51 are provided behind the observation window 31, and the image pickup device 33 is located in a position where the plurality of lenses 30 form an image.

The lens frames 51 and the image pickup device 33 are held by a fixing frame 120, which is provided between the lens frames 51 and the image pickup device 33 in the longitudinal direction N.

The fixing frame 120 holds the internal unit 150 and is made of a metal to dissipate heat in the image pickup device 33.

The fixing frame 120 has one or more fixing portions 120y, which are not shown but fix the internal unit 150 to an inner surface 17n of the main cover 17a (FIG. 3 shows only one fixing portion 120y), as shown in FIG. 3.

The fixing portion 120y has a through hole that is not shown but passes through the fixing portion 120y in the longitudinal direction N, and a screw 60 inserted through the through hole engages with a threaded hole 16, which is formed on the inner surface 17n, via a washer that is not shown but is coated on an outer circumference of the screw 60. The fixing portion 120y is therefore fixed to the inner surface 17n via the metal.

That is, the fixing frame 120 is fixed to the inner surface 17n.

Further, in the interior 17i of the exterior member 17, a variety of substrates, which are held by a substrate holder 200, which is bent in an L-letter shape, and are electrically connected to the image pickup device 33, are provided behind the image pickup device 33, as shown in FIG. 3.

The variety of substrates are electrically connected to a substrate 35, which is located behind the substrate holder 200, via a flexible substrate 138 bent in a U-letter shape.

The substrate holder 200 and the substrate 35 are fixed to a frame 28, which is fixed to an outer circumference of the fixing frame 120.

A connector 38a on a flexible substrate 38, which extends from the substrate 35 and is so folded in an inverted U-letter shape as compared with the erect U-letter shape of the flexible substrate 138, is electrically connected to the substrate 35.

A connector 38b, which is provided at an extended end of the flexible substrate 38, is electrically connected to a substrate 320, which is located behind the substrate 35 and so provided as to incline with respect to the substrate 35.

A hermetic connector 160, which is fixed to the inner surface 17n of an end portion of the rear cover 17b, for example, in a soldering process, is provided at the proximal end of the substrate 320, and a substrate 45 is provided at a proximal end of the hermetic connector 160.

The hermetic connector 160 is provided with a plurality of conduction pins 42, which pass through the hermetic connector 160, and the conduction pins 42 electrically connect the substrate 320 to the substrate 45.

A distal end of a cable fixing frame 41, which is made of a metal, is connected to a proximal end of the rear cover 17b via the hermetic connector 160, as shown in FIG. 3.

Further, a spacer ring 179 is fixed to a proximal end of the cable fixing frame 41, and a distal end of the camera cable 12 is connected to an inner circumferential surface of the spacer ring 179.

A plurality of electric cords, which are each formed of a metal conductor surrounded, for example, by a resin material, are accommodated in the camera cable 12, and a distal end of each of the electric cords extends into the cable fixing frame 41 and is electrically connected to the substrate 45.

A bending stopper 44, which prevents the camera cable 12 from being abruptly bent, is coated around an outer circumferential surface of the camera cable 12. A rear screw 50 movably covers the outer circumference of the bending stopper 44, and the rear screw 50 watertightly and airtightly fixes the distal end of the camera cable 12 to the cable fixing frame 41.

Further, an exterior cover 40, which is made of Redel (registered trademark), PEEK, or any other resin material, is so provided as to cover an outer circumference of the rear cover 17b and an outer circumference of the proximal end of the cable fixing frame 41 over a portion from a distal end of the rear cover 17b to a distal end of the rear screw 50.

The configuration of the switch unit 270 will next be described with reference to FIGS. 2 to 4.

Figure 4:
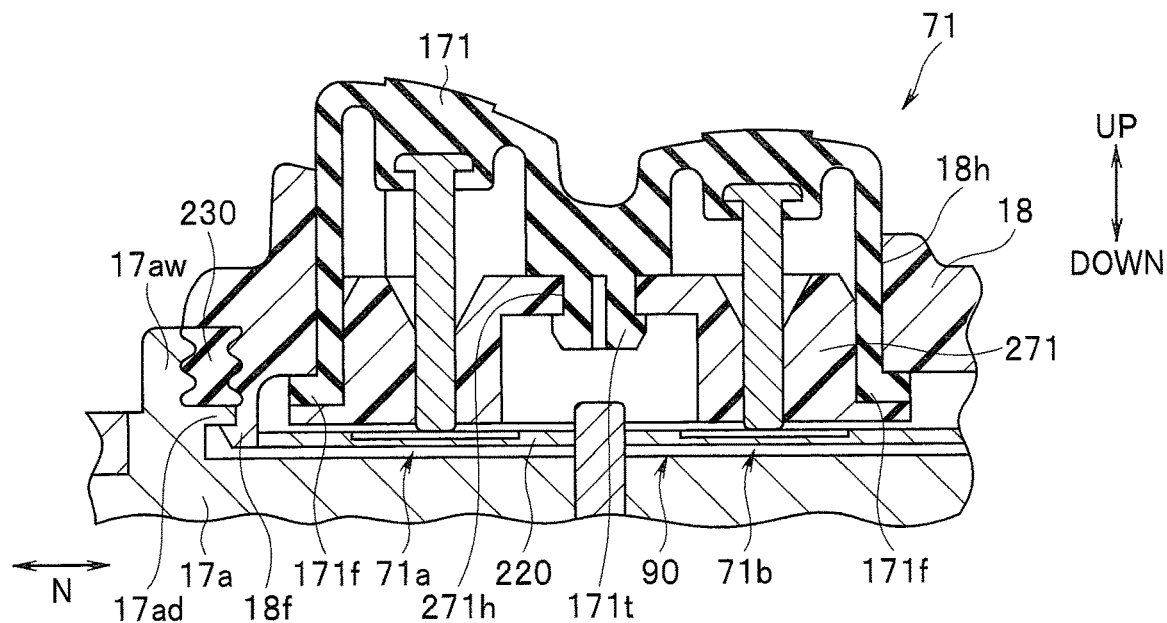
FIG. 4 is an enlarged partial cross-sectional view of a portion enclosed with a line IV in the camera head in FIG. 3.

As shown in FIGS. 2 to 4, an opening section 90 is formed in the outer surface 17ag of an upper portion of the main cover 17a in FIGS. 2 to 4. The opening section 90 has a predetermined size and a predetermined depth in the UP-DOWN direction shown in FIGS. 2 to 4, and the circumference of the opening section 90 is covered with a wall section 17aw, which rises from the outer surface 17ag of the upper portion of the main cover 17a in an UP direction.

The opening section 90 does not communicate with the interior 17i of the exterior member 17, and the outer surface 17ag of the upper portion of the main cover 17a forms a bottom portion of the opening section 90.

The switch unit 270 is fit into and watertightly fixed to the opening section 90.

The switch unit 270 is primarily formed of a plurality of switch buttons 71 to 75, a switch button frame 18, which is a frame body that watertightly attaches the plurality of switch buttons 71 to 75 to the opening section 90 via a watertight member 230, and a substrate 220, as shown in FIG. 3.

The switch button 71 is a focus adjusting button that is formed of a proximal point button and a distal point button integrated with each other and moves part of the lenses 30 frontward or rearward for focus adjustment.

The switch button 71 includes a distal point switch 71a, a proximal point switch 71b, which is so provided as to be separate from the distal point switch 71a in the longitudinal direction N, and a switch fixing member 271, which fixes the distal point switch 71a and the proximal point switch 71b to the opening section 90 and provides watertightness.

The switch button 71 further includes a single soft switch cover 171, which covers the distal point switch 71a, the proximal point switch 71b, and the switch fixing member 271.

The switch button 72 is a zoom button that is formed of a Wide button and a Tele button integrated with each other and moves part of the lenses 30 frontward or rearward for focus/magnification adjustment.

The switch button 72 includes a Wide switch that is not shown, a Tele switch that is not shown but is so provided as to be separate from the Wide switch in a direction substantially orthogonal to the longitudinal direction N, and a switch fixing member 272, which fixes the Wide switch and the Tele switch to the opening section 90 and provides watertightness.

The switch button 72 further includes a single soft switch cover 172, which covers the Wide switch, the Tele switch, and the switch fixing member 272.

The switch button 73 is a brightness adjusting button and is primarily formed of a switch that is not shown, a switch fixing member that is not shown but fixes the switch to the opening section 90 and provides watertightness, and a single soft switch cover 173, which is not shown but covers the switch and the switch fixing member.

The switch button 74 is a color adjusting button and is primarily formed of a switch that is not shown, a switch fixing member that is not shown but fixes the switch to the opening section 90 and provides watertightness, and a single soft switch cover 174, which is not shown but covers the switch and the switch fixing member.

The switch cover 174 is so fastened around an outer circumference of the switch fixing member for the switch button 74 that the outer circumference fits therein.

The switch button 75 is a release button and is primarily formed of a switch 75a, a switch fixing member 275, which fixes the switch 75a to the opening section 90 and provides watertightness, and a single soft switch cover 175, which covers the switch 75a and the switch fixing member 275.

The switch cover 175 is so fastened around an outer circumference of the switch fixing member 275 that the outer circumference fits therein.

The switch button frame 18 is made, for example, of a resin, covers DOWN-direction-side part of the variety of switch covers 171 to 175, which cover the switch buttons 71 to 75, in such a way that UP-direction-side part of the switch covers 171 to 175 are exposed, and watertightly fixes the variety of switch covers 171 to 175.

As an example, an outward flange 171f, which is provided around an outer circumference of a DOWN-direction-side bottom portion of the switch cover 171, is caught by an opening end of a DOWN-side bottom portion of a fitting hole 18h, into which the switch button 71 caught by the switch button frame 18 is fit, as shown in FIG. 4.

The switch cover 171 is therefore watertightly fixed to the switch button frame 18. The watertight configuration of the switch cover 171 described above also applies to the variety of switch covers 172 to 175.

The switch button frame 18 is so configured that an outer circumferential surface of a cover portion that covers the variety of switch covers 171 to 175 watertightly abuts against an inner circumferential surface of the wall section 17aw via the watertight member 230 having an annular shape, as shown in FIG. 4.

The switch button frame 18 is watertightly fixed to the opening section 90. Specifically, the switch button frame 18 is so configured that a plurality of elastically deformable claw sections 18f (FIG. 4 shows only one claw section 18f), which are provided at set intervals in an outer circumferential direction around an outer circumference of a DOWN-direction-side bottom portion of the cover portion, are caught in snap fitting by a catching protrusion 17ad, which is so provided as to protrude inward from the wall section 17aw into the opening section 90.

Further, the switch button frame 18 is fixed to the outer surface 17ag of the upper portion of the main cover 17a with a single screw 19. The switch button frame 18 is therefore watertightly fixed to the opening section 90.

The substrate 220 is electrically connected to the substrates provided in the interior 17i of the exterior member 17 and held by the substrate holder 200 via a hermetic connector 310 (see FIG. 11), which will be described later.

A catch section of the switch cover 171 caught by the switch fixing member 271 is provided between the distal point switch 71a and the proximal point switch 71b.

The reason for this is to prevent, for example, the switch cover 171 in the position between the distal point switch 71a and the proximal point switch 71b of the switch button 71 from moving upward or downward due to negative or positive pressure in the switch cover 171 that occurs, for example, in the autoclave process.

Specifically, the catch section is formed of a convex claw section 171t, which protrudes from the position between the distal point switch 71a and the proximal point switch 71b toward the switch fixing member 271 in the DOWN direction, in the switch cover 171, as shown in FIG. 4.

The claw section 171t passes in the UP-DOWN direction through a through hole 271h, which is so formed in a position facing the claw section 171t as to pass through the switch fixing member 271 in the UP-DOWN direction, and is caught by the switch fixing member 271.

The configuration in which the claw section 171t catches the switch fixing member 271 prevents, for example, the switch cover 171 in the position between the distal point switch 71a and the proximal point switch 71b of the switch button 71 from moving upward or downward due to negative or positive pressure in the switch cover 171.

A convex claw section 172t, which is a catch section provided as part of the switch fixing member 272, prevents the switch cover 172 between the Wide switch and the Tele switch of the switch button 72 from moving upward or downward.

The shape and catching configuration of the claw section 172t are the same as the shape and catching configuration of the claw section 171t.

The other configuration of the camera head 3 is known and will not therefore be described.

As described above, in the present embodiment, the switch button 71 is a focus adjusting button that is formed of the proximal point button and the distal point button integrated with each other and moves part of the lenses 30 frontward or rearward for focus adjustment.

The switch button 72 is a zoom button that is formed of the Wide button and the Tele button integrated with each other and moves part of the lenses 30 frontward or rearward for focus/magnification adjustment, as described above.

The catch section of the switch cover 171, which is caught by the switch fixing member 271, is provided between the distal point switch 71a and the proximal point switch 71b of the switch button 71, as described above.

Specifically, the catch section is formed of the convex claw section 171t, which protrudes from the position between the distal point switch 71a and the proximal point switch 71b toward the switch fixing member 271 in the DOWN direction, in the switch cover 171, as described above.

The claw section 171t passes through the through hole 271h, which is formed in the switch fixing member 271, and is caught by the switch fixing member 271, as described above.

The configuration in which the claw section 171t, which is provided as part of the switch cover 171, catches the switch fixing member 271 prevents the switch cover 171 in the position between the distal point switch 71a and the proximal point switch 71b of the switch button 71 from moving upward or downward due to negative or positive pressure in the switch cover 171 in the autoclave process carried out on the camera head 3 even in a case where the proximal point button and the distal point button are integrated with each other so that the surface area of the switch button 71 increases.

Similarly, the convex claw section 172t, which is the catch section of the switch cover 172 that is caught by the switch fixing member 272, is provided between the Wide switch and the Tele switch of the switch button 72, as described above.

The configuration in which the claw section 172t, which is provided as part of the switch cover 172, catches the switch fixing member 272 prevents the switch cover 172 in the position between the Wide switch and the Tele switch of the switch button 72 from moving upward or downward due to negative or positive pressure in the switch cover 172 in the autoclave process carried out on the camera head 3 even in a case where the Wide button and the Tele button are integrated with each other so that the surface area of the switch button 72 increases, as in the case of the switch button 71.

As described above, the present embodiment can provide the switch unit 270, which has the configuration that prevents an inter-switch portion of a switch cover that covers a plurality of switches from moving upward or downward due to negative or positive pressure in the watertightly maintained interior of the switch cover, the camera head 3 including the switch unit 270, and the endoscope 2 including the switch unit 270.

Figure 5:
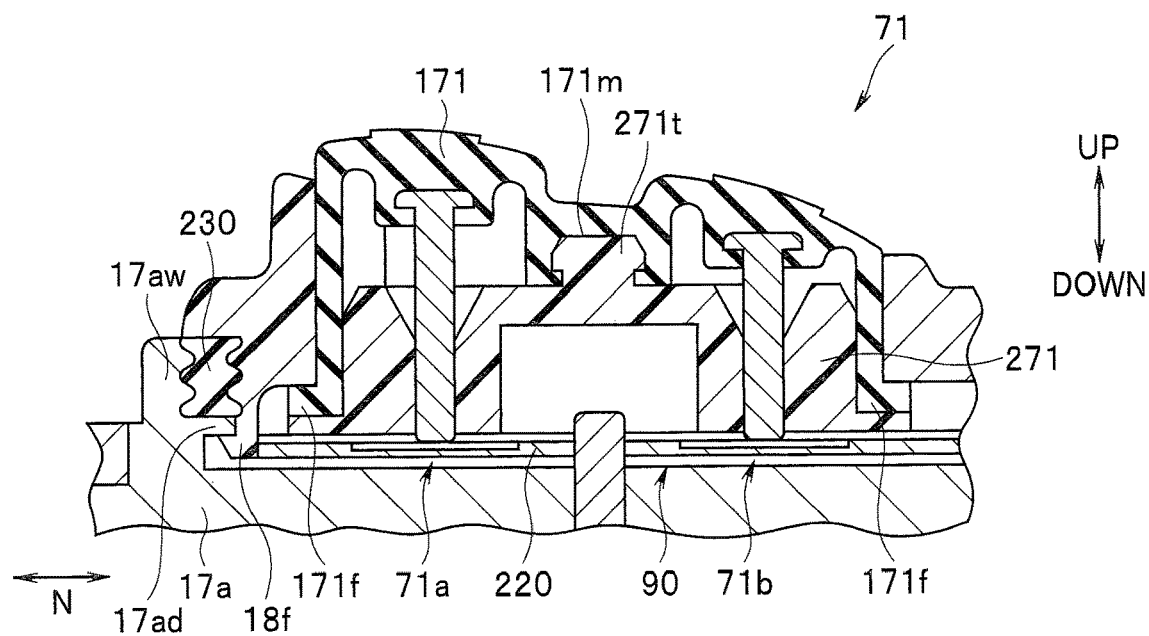
FIG. 5 is a partial cross-sectional view showing a modification in which a switch fixing member is provided with the catch section in FIG. 4.

A modification will be described below with reference to FIG. 5. FIG. 5 is a partial cross-sectional view showing a modification in which the switch fixing member is provided with the catch section in FIG. 4.

In the present embodiment described above, the catch section that is part of the switch cover 171 and caught by the switch fixing member 271 is provided between the distal point switch 71a and the proximal point switch 71b of the switch button 71.

The catch section is formed of the convex claw section 171t, which protrudes from a position between the distal point switch 71a and the proximal point switch 71b in the DOWN direction toward the switch fixing member 271 in the switch cover 171, as described above.

The catch section is not limited to be configured as described above. The catch section in the switch button 71 may be formed of a convex claw section 271t, which is part of the switch fixing member 271, protrudes in the UP direction toward the switch cover 171, and is caught by a concave groove 171m formed in the switch cover 171, as shown in FIG. 5.

Although not shown, the catch section in the switch button 72 may similarly be formed of a convex claw section that is part of the switch fixing member 272, protrudes in the UP direction toward the switch cover 172, and is caught by a concave groove formed in the switch cover 172.

The configuration described above can also provide the same effect as the effect provided by the present embodiment described above.

Figure 6:
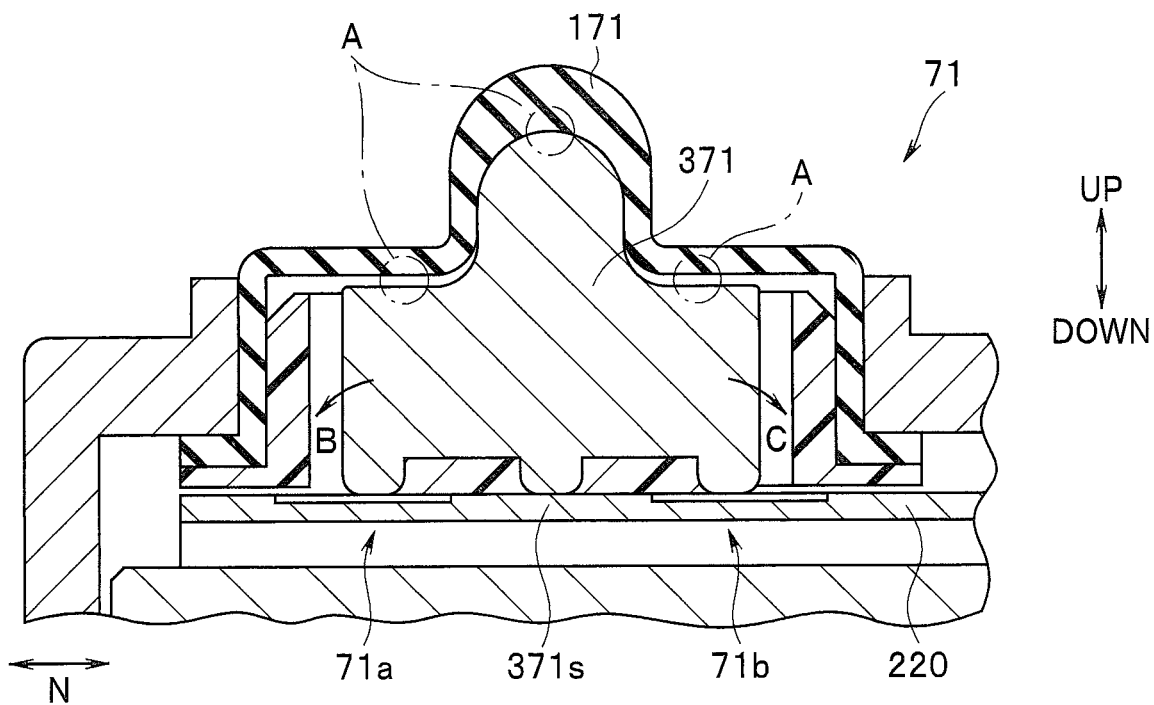
FIG. 6 is a partial cross-sectional view showing a modification in which either of the catch sections in FIGS. 4 and 5 is used in a seesaw-type button.

Another modification will be described below with reference to FIG. 6. FIG. 6 is a partial cross-sectional view showing a modification in which either of the catch sections in FIGS. 4 and 5 is used in a seesaw-type button.

The catch section that is part of the switch cover 171 and caught by the switch fixing member 271 shown in FIG. 4 and the catch section that is part of the switch fixing member 271 and caught by the switch cover 171 shown in FIG. 5 can also be used in a case where the switch button 71 has a seesaw-type button structure.

Specifically, FIG. 6 shows a switch terminal 371, which is so operated via the switch cover 171 as to incline in a direction B or C around a pivotal point 371s, which is in contact with the substrate 220, and using the catch section shown in either of FIGS. 4 and 5 in portions enclosed with lines A in FIG. 6 that are portions that come into contact with the switch cover 171 can also provide the same effect as the effect provided by the present embodiment described above.

The configuration of the seesaw-type button shown in FIG. 6 can, of course, be used as the configuration of the switch button 72.

Further, in the present embodiment described above, the switch buttons 71 and 72 each having two switches have been presented by way of example, but not necessarily, and the switch buttons 71 and 72 may, of course, each have three or more switches.

Figure 7:
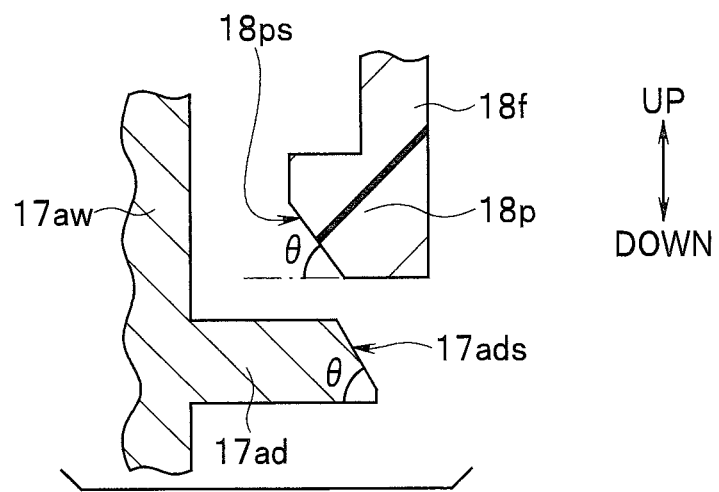
FIG. 7 is a partial cross-sectional view showing a modification of the shape of claw sections of a switch button frame in FIG. 3 and further showing part of a main cover.
Figure 8:
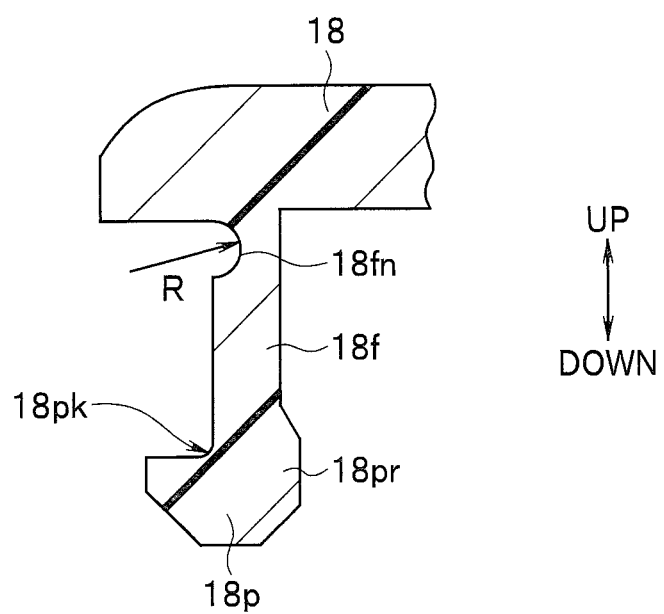
FIG. 8 is a partial cross-sectional view showing a modification of the shape of the claw sections of the switch button frame in FIG. 3 different from the shape shown in FIG. 7.

FIG. 7 is a partial cross-sectional view showing a modification of the shape of the claw sections of the switch button frame shown in FIG. 3 and further showing part of the main cover, and FIG. 8 is a partial cross-sectional view showing a modification of the shape of the claw sections of the switch button frame shown in FIG. 3 different from the shape shown in FIG. 7.

In consideration of attachment of the switch unit 270 to the opening section 90, it is usually preferable that the switch button frame 18 in which the switch buttons 71 to 75 have been incorporated in the fitting hole 18h in advance is fixed into the opening section 90 with the screw 19.

However, to improve the watertightness between the switch button frame 18 and the opening section 90, the number of screws 19 needs to be increased, resulting in a problem of compromise of the exterior appearance.

Further, in a case where the switch button frame 18 has a complicated outer circumferential shape, fixing the switch button frame 18 with the screw 19 does not allow the switch button frame 18 to apply uniform pressure to the watertight member 230 provided around the circumference of the switch button frame 18.

It is therefore undesirably difficult to ensure the watertightness between the switch button frame 18 and the opening section 90.

In view of the circumstances described above, only one screw 19 is used to fix the switch button frame 18 to the opening section 90 in the present embodiment described above.

Further, the plurality of claw sections 18f are caught in snap fitting by the catching protrusions 17ad, which are so provided as to protrude from the wall section 17aw inward into the opening section 90, as described above.

In the configuration using the plurality of claw sections 18f as described above, the configuration in which the plurality of claw section 18f are caught by the catching protrusions 17ad allows the switch button frame 18 to apply uniform pressure to the annular watertight member 230 even in the case where only one screw 19 is used.

Further, since not only is only one screw 19 used but the plurality of claw sections 18f are not exposed through an outer surface of the switch button frame 18, the exterior appearance of the camera head 3 can be improved.

In the configuration using the plurality of claw sections 18f, an inclining surface that inclines by an angle θ may be formed as not only a contact surface 18ps of a catch section 18p of each of the claw sections 18f, which comes into contact with the corresponding catching protrusion 17ad, but a contact surface 17ads of each of the catching protrusions 17ad, which comes into contact with the corresponding catch section 18p.

In this configuration, when the contact surfaces 18ps are caused to be in contact with the contact surfaces 17ads and pass in the DOWN direction to cause the catch sections 18p to be caught by the catching protrusions 17ad, the contact surfaces 18ps slide along the contact surfaces 17ads in a more satisfactory manner, resulting in more satisfactory passage of the catch sections 18p.

It is further conceivable to form an arcuate recess 18fn at a base portion of an upper portion, in the UP direction, of each of the claw sections 18f. In this case, the claw sections 18f are readily flexed when the catch sections 18p are caught by the catching protrusions 17ad, as shown in FIG. 8. That is, the claw sections 18f are likely to be elastically deformed.

Increasing the radius R of the arc of each of the recesses 18fn allows reduction in the magnitude of stress induced when the claw section 18f is flexed.

Further, since the arc of a portion 18pk of each of the catch sections 18p, which is caught by the corresponding catching protrusion 17ad, cannot have a large radius in consideration of the diameter of the claw sections 18f, a rib 18pr may be formed on each of the catch sections 18p, as shown in FIG. 8.

Figure 9:
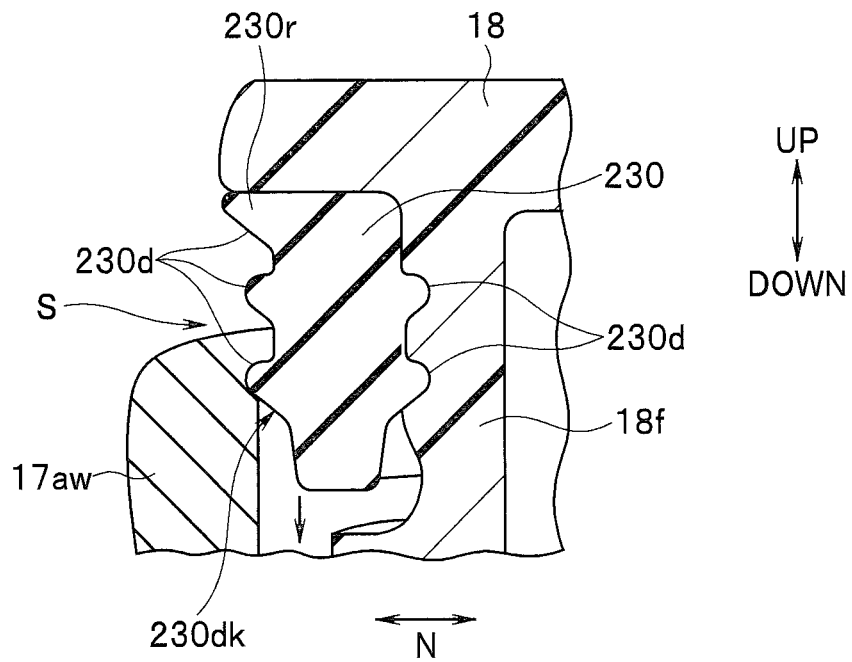
FIG. 9 is a partial cross-sectional view showing a modification of the shape of a watertight member before assembled as shown in FIG. 3 and further showing part of the switch button frame and the main cover.
Figure 10:
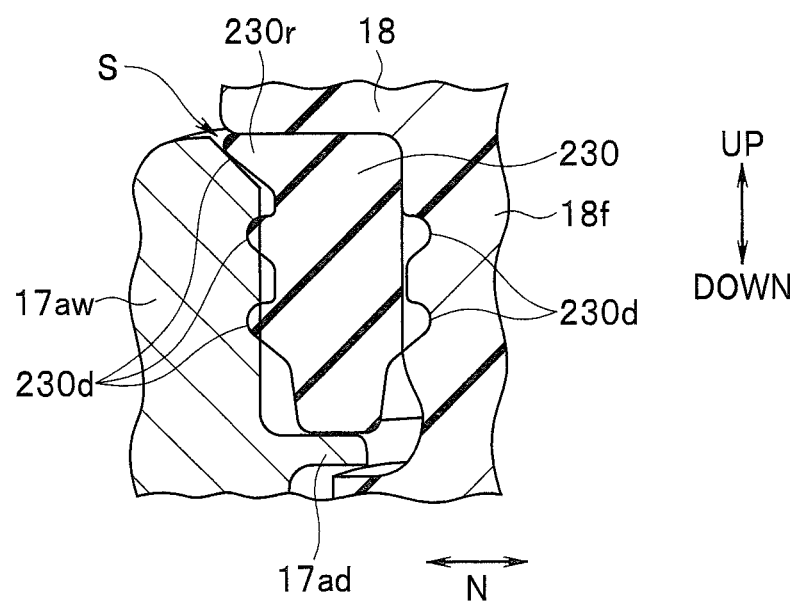
FIG. 10 is a partial cross-sectional view showing the state of the assembled watertight member in FIG. 9 and further showing part of the switch button frame and the main cover.

FIG. 9 is a partial cross-sectional view showing a modification of the shape of the watertight member before assembled as shown in FIG. 3 and further showing part of the switch button frame and the main cover, and FIG. 10 is a partial cross-sectional view showing the state of the assembled watertight member in FIG. 9 and further showing part of the switch button frame and the main cover.

The switch button frame 18 is watertightly attached to the opening section 90 via the watertight member 230, as shown in FIG. 3 described above.

As the configuration of the watertight member 230, to improve the watertightness, there is a known configuration having a roughly rectangular cross-sectional shape having a plurality of protrusions 230d formed along an outer circumference of the watertight member 230 so that a large crush margin is provided, as shown in FIGS. 9 and 10.

In the case of the watertight member 230 having the plurality of protrusions 230d along the outer circumference, an inclining surface 230dk is formed on each of the protrusions 230d in the present configuration, as shown in FIG. 9.

The inclining surfaces 230dk allow reduction in passage resistance of the watertight member 230 that occurs when the watertight member 230 is crushed in the DOWN direction and the switch button frame 18 is attached to the opening section 90, whereby the insertability of the watertight member 230 can be improved.

Further, since the protrusions 230d are readily crushed, the switch button frame 18 can be attached to the opening section 90 with smaller force than force required in related art.

Further, in the present configuration, a rib 230r is formed as one of the protrusions 230d of the watertight member 230 in a position facing a gap S, which is created in the course of the attachment of the switch button frame 18 to the opening section 90 and which is exposed through the exterior appearance.

In the configuration described above, after the switch button frame 18 is attached to the opening section 90, the rib 230r is crushed and fills the gap S, whereby a portion close to the gap S can be cleaned and disinfected in an improved manner as shown in FIG. 10.

Figure 11:
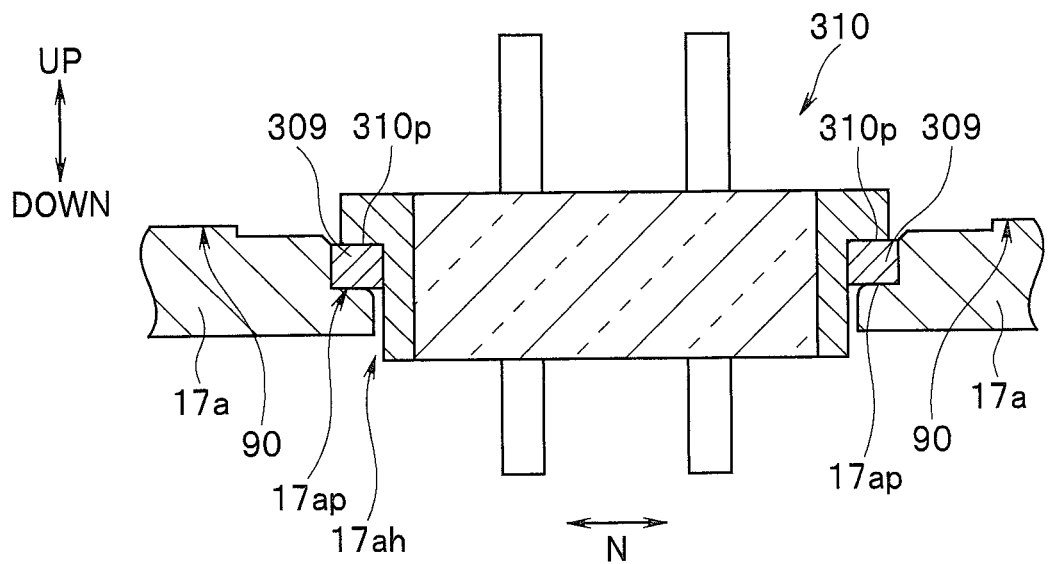
FIG. 11 is a partial cross-sectional view schematically showing a hermetic connector fixing configuration of related art enclosed with a line XI in FIG. 3.
Figure 12:
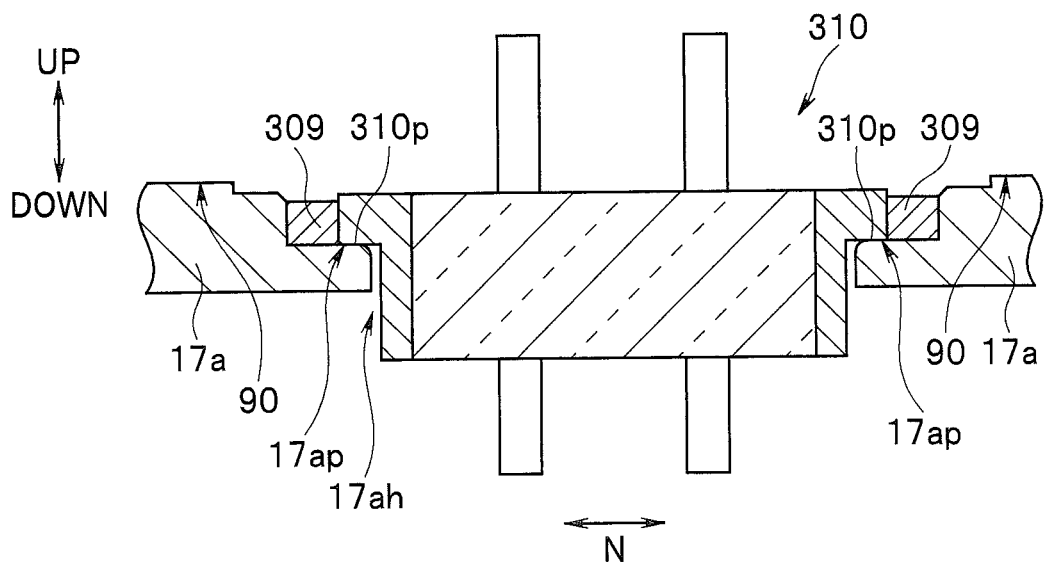
FIG. 12 is a partial cross-sectional view schematically showing a hermetic connector fixing configuration of the present embodiment.

FIG. 11 is a partial cross-sectional view schematically showing a hermetic connector fixing configuration of related art enclosed with a line XI in FIG. 3, and FIG. 12 is a partial cross-sectional view schematically showing a hermetic connector fixing configuration of the present embodiment.

As shown in the present embodiment described above, the substrate 220 of the switch unit 270 is electrically connected to the substrates fixed to the substrate holder 200 in the interior 17*i* of the exterior member 17 via the hermetic connector 310.

As a method for fixing the hermetic connector 310 and the configuration of the hermetic connector 310, a stepped section 310*p* of the hermetic connector 310 is caused to come into contact with a stepped section 17*ap* of an insertion hole 17*ah*, which is formed in a portion that communicates with the opening section 90 in an upper portion of the main cover 17*a* in such a way that the opening section 90 communicates with the interior 17*i*, via ring-shaped solder 309, as shown in FIG. 11.

The solder 309 is then melted to cause the hermetic connector 310 to fall in the DOWN direction to a position where the stepped section 310*p* comes into contact with the stepped section 17*ap* to achieve airtight sealing. The above approach and configuration are known.

In the approach and the configuration described above, however, the hermetic connector 310 does not fall to a point where the stepped section 310*p* completely comes into contact with the stepped section 17*ap* but the hermetic connector 310 stops in a halfway position in some cases.

Further, airtight sealing is achieved with the hermetic connector 310 inclining in some cases. The quality of the sealing of the hermetic connector 310 (strength, airtightness) therefore deteriorates in some cases.

In view of the circumstances described above, in the present configuration, the following approach and configuration are used: After the stepped section 310*p* completely comes into contact with the stepped section 17*ap*, an outer circumference of the stepped section 310*p* is fixed to the insertion hole 17*ah* by using ring-shaped solder 309, as shown in FIG. 12.

According to the configuration described above, the state in which the stepped section 310*p* is in contact with the stepped section 17*ap* does not change after the solder 309 is melted.

In the configuration described above, the hermetic connector 310 will not incline, or the position of the hermetic connector 310 in the UP-DOWN direction will not change.

Figure 13:
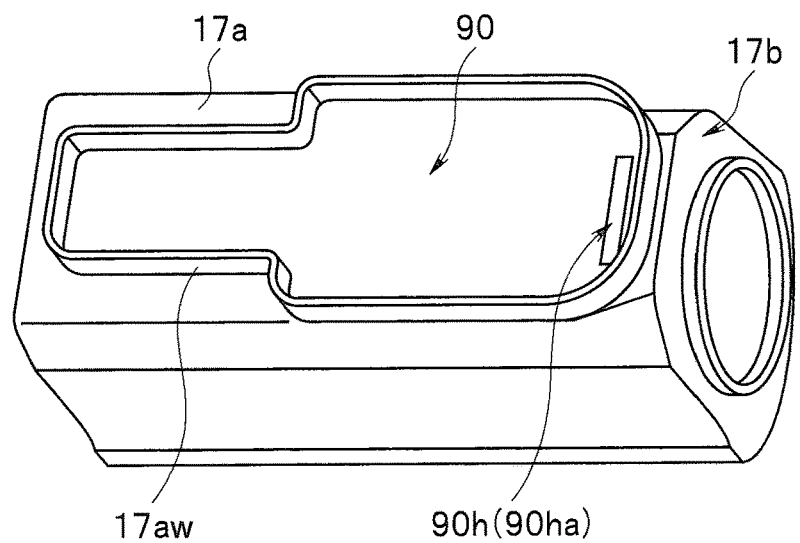
FIG. 13 is a perspective view of an exterior member in FIG. 3, which is of a front-side sealing type.
Figure 14:
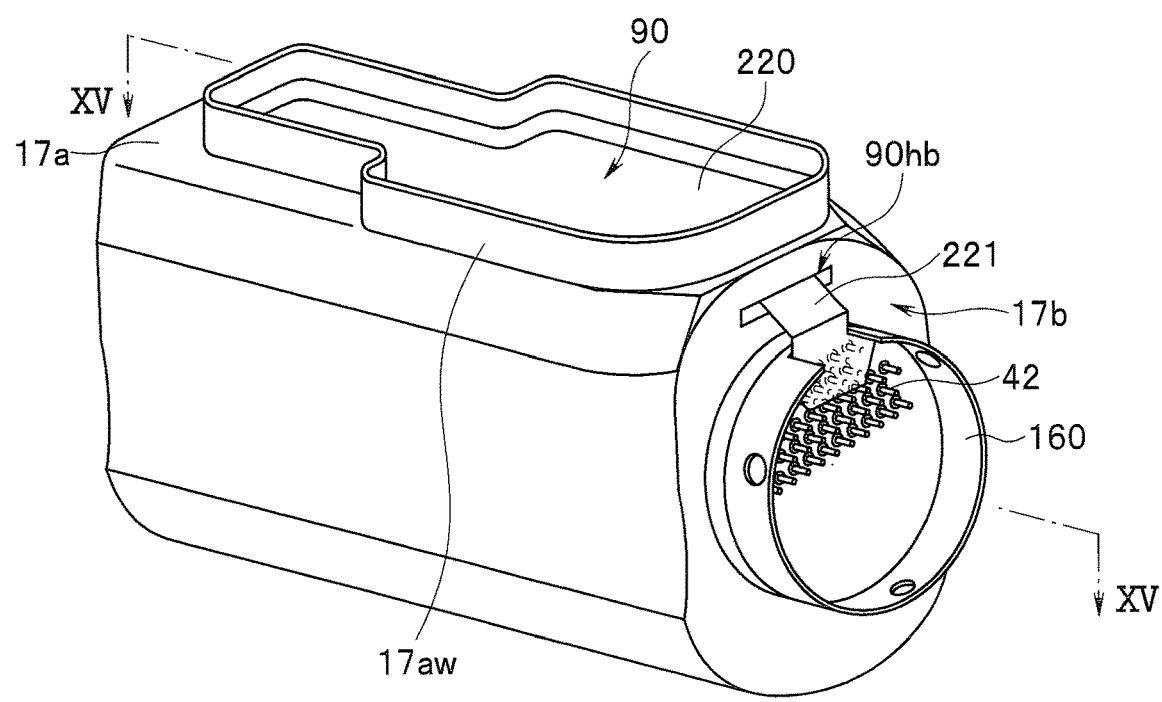
FIG. 14 is a perspective view showing a substrate extracting configuration using no hermetic connector in which a substrate is extracted through an opening section of an airtight enclosure in FIG. 13.
Figure 15:
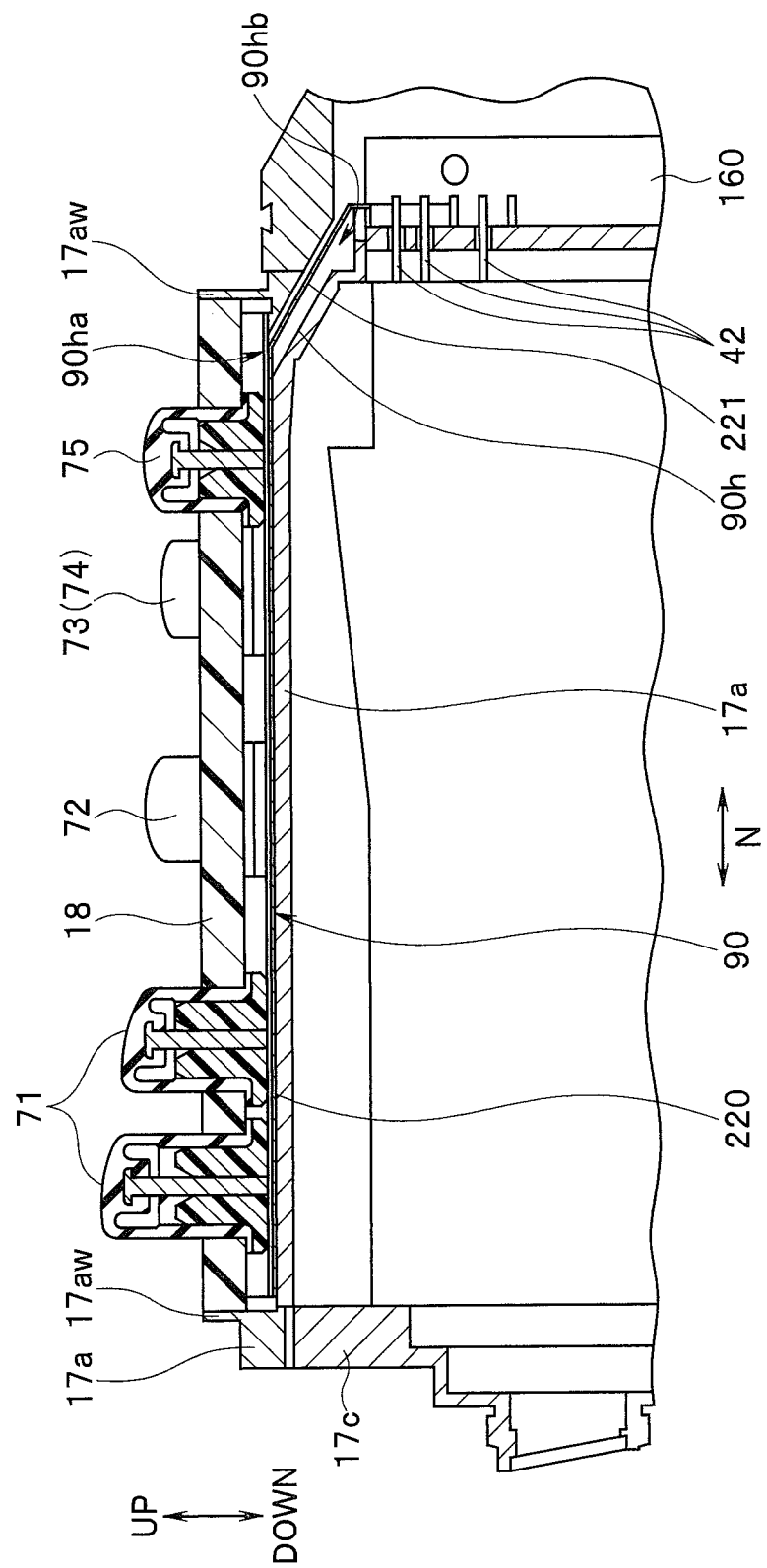
FIG. 15 is a partial cross-sectional view taken along a line XV-XV in FIG. 14 with a front cover fixed to a main cover in FIG. 14.

FIG. 13 is a perspective view of the exterior member in FIG. 3, which is of a front-side sealing type. FIG. 14 is a perspective view showing a substrate extracting configuration using no hermetic connector in which a substrate is extracted through an opening section of an airtight enclosure in FIG. 13. FIG. 15 is a partial cross-sectional view taken along a line XV-XV in FIG. 14 with a front cover fixed to a main cover in FIG. 14.

In the present embodiment described above, in which the proximal end of the main cover 17*a* is sealed with the rear cover 17*b*, the interior 17*i* of the exterior member 17 is watertightly and airtightly sealed.

The configuration described above is not necessarily employed. It is conceivable to employ a configuration in which the interior 17*i* is watertightly and airtightly sealed by sealing a distal end of the main cover 17*a* shown in FIG. 13 with a front cover 17*c*, as shown in FIG. 15.

In the configuration described above, it is conceivable to employ a configuration using no hermetic connector 310 in which the substrate 220 is shifted rearward from the opening section 90 and a flexible extension substrate 221 is used to electrically connect the substrate 220 to the conduction pins 42 of the hermetic connector 160.

The configuration described above, however, not only causes an increase in the area of the substrate 220 and the extension substrate 221 exposed through the exterior appearance over a portion from the opening section 90 to the hermetic connector 160 but causes an exterior shape of the exterior member to be complicated.

It is therefore undesirably difficult to ensure the watertightness of the switch unit 270.

To solve the problem described above, it is conceivable to employ a configuration in which the opening section 90 is covered with the wall section 17*aw* to ensure the watertightness of only the opening section 90 so that the exterior shape of the exterior member is simplified and the watertightness of the switch unit 270 is readily ensured, as shown in the present embodiment described above and FIG. 13.

In the configuration described above, it is conceivable to employ configurations shown in FIGS. 13 to 15 using no hermetic connector 310 as the configuration that connects the substrate 220 to the conduction pins 42.

Specifically, it is conceivable to employ a configuration in which the main cover 17*a* has an inclining hole 90*h*, which has one end that opens as an opening 90*ha* to the opening section 90 and the other end that opens as an opening 90*hb* through the rear cover 17*b*, which seals the proximal end of the main cover 17*a*, and the extension substrate 221 is extracted through the opening section 90 via the inclining hole 90*h*.

According to the configuration described above, the extension substrate 221, which extends from the substrate 220, can be extracted via the inclining hole 90*h* to a position outside the opening section 90 but behind the rear cover 17*b* and electrically connected to the conduction pins 42.

As a result, the same watertightness of the switch unit 270 as the watertightness in the case where the hermetic connector 310 is used can be ensured.

Figure 16:
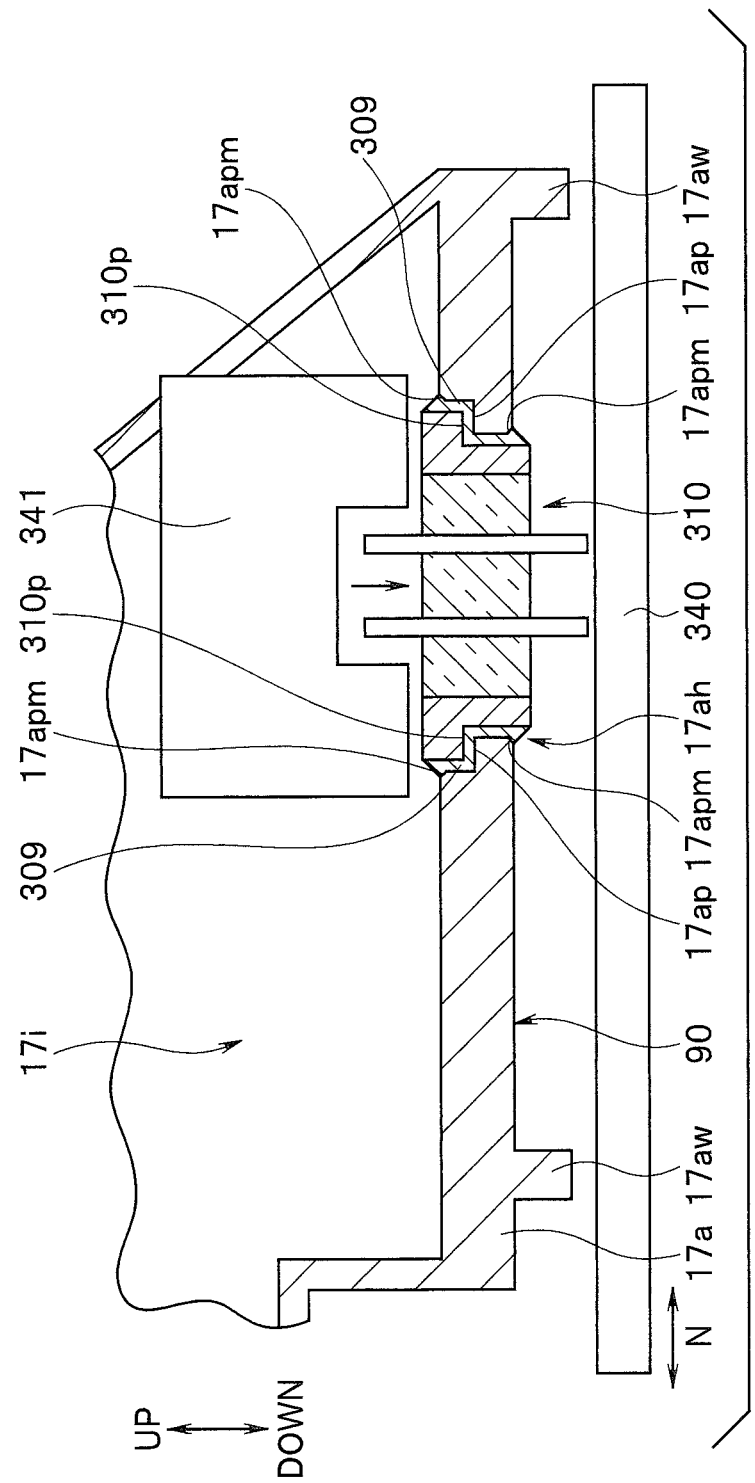
FIG. 16 is a partial cross-sectional view schematically showing a method for fixing the hermetic connector to the main cover in FIG. 3.
Figure 17:
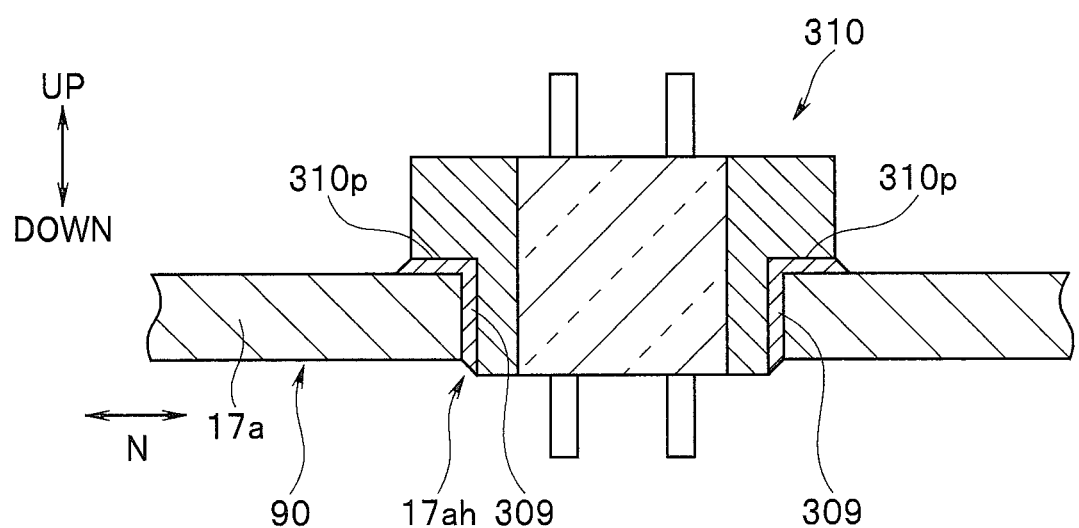
FIG. 17 is a partial cross-sectional view showing a modification in which an insertion hole of the main cover in FIG. 16 is formed in a shape having no stepped section and further showing the hermetic connector.

FIG. 16 is a partial cross-sectional view schematically showing a method for fixing the hermetic connector to the main cover in FIG. 3, and FIG. 17 is a partial cross-sectional view showing a modification in which an insertion hole of the main cover in FIG. 16 is formed in a shape having no stepped section and further showing the hermetic connector.

The hermetic connector 310 is fixed to the insertion hole 17*ah* of the main cover 17*a* via the solder 309, as shown in FIGS. 11 and 12 described above.

Further, the hermetic connector 310 is fixed in the main cover 17*a* and on the side in the UP direction, as shown in FIG. 3.

However, when the hermetic connector 310 is fixed along the UP direction by using the solder 309 with the hermetic connector 310 oriented in the UP direction, the self-weight of the hermetic connector 310 is likely to cause known flux used along with the solder 309 to enter the interior 17*i*.

As a result, since the interior 17*i* is likely to erode, the flux in the interior 17*i* needs to be wiped off after the fixation using the solder. It is, however, difficult to wipe off wet flux in the interior 17*i*.

To solve the problem, when the hermetic connector 310 is fixed to the insertion hole 17*ah* by using the solder 309, the exterior member 17 may be inverted upside down in the UP-DOWN direction, and a fixing jig 341 may be used in the interior 17*i* to urge the hermetic connector 310 to a hot plate 340, which melts the solder 309, to fix the hermetic connector 310, as shown in FIG. 16.

In the procedure described above, formation of an inclining surface at an annular opening end 17*apm* of the insertion hole 17*ah* allows the state of a solder pool to be visible, whereby the operator can readily visually recognize whether or not the solder is satisfactorily bonded.

Since the distance between the hot plate 340 and the solder 309 is short, heat transfer from the hot plate 340 to the solder 309 is improved.

Further, since the flux does not leak into the interior 17*i* but leaks toward the opening section 90, the amount of flux that enters the interior 17*i* can be reduced, and the flux can be more readily wiped off.

A configuration shown in FIG. 17 may be employed: The insertion hole 17*ah* has no stepped section 17*ap*, and the stepped section 310*p* of the hermetic connector 310 abuts against a portion close to the opening end of the insertion hole 17*ah* in the interior 17*i*.

Figure 18:
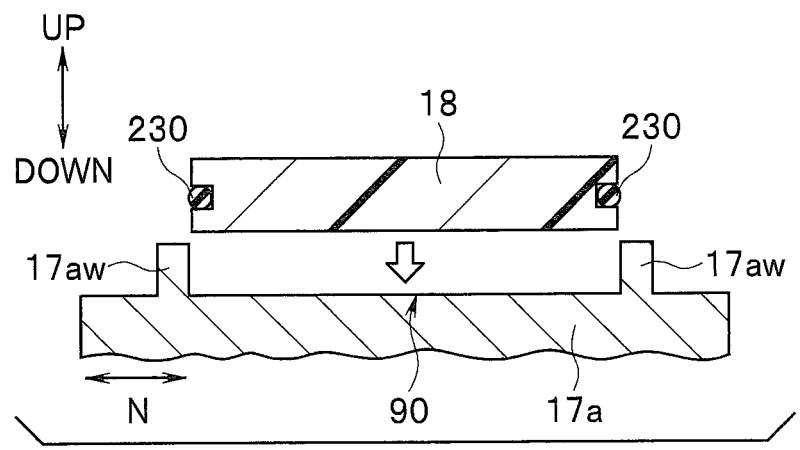
FIG. 18 is a partial cross-sectional view schematically showing a configuration in which an annular watertight member is provided on an outer circumferential surface of the switch button frame in FIG. 3 and further showing part of the main cover.
Figure 19:
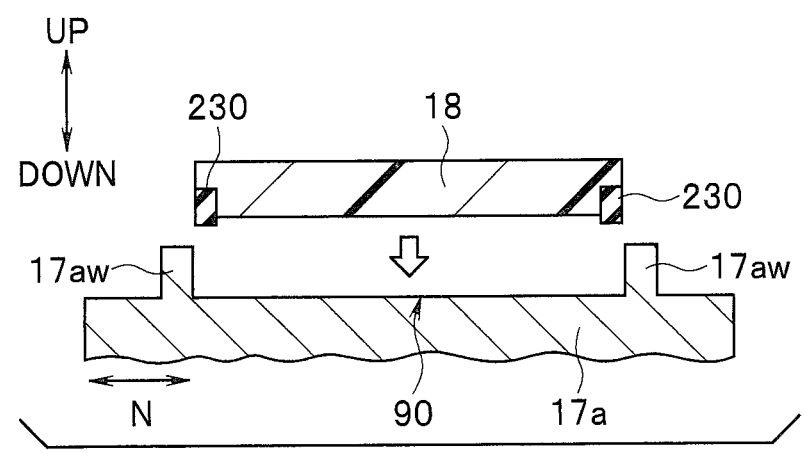
FIG. 19 is a partial cross-sectional view schematically showing a configuration in which the watertight member in FIG. 18 is provided on a bottom surface of the switch button frame.
Figure 20:
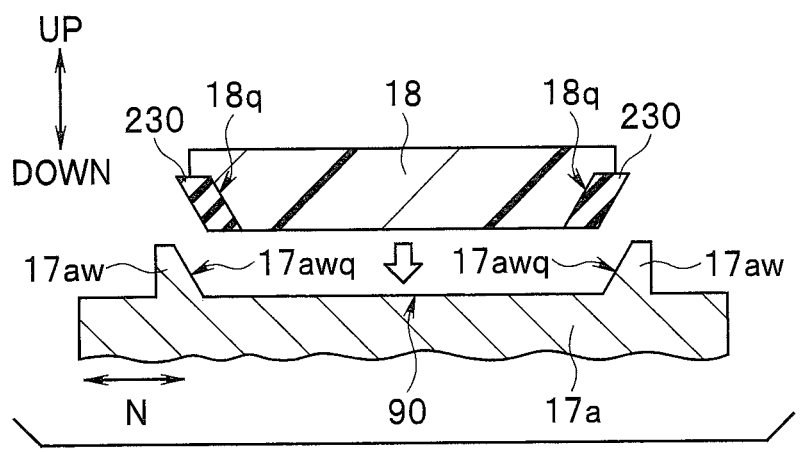
FIG. 20 is a partial cross-sectional view schematically showing a configuration in which the watertight member in FIG. 19 is provided on an inclining surface that connects the outer circumferential surface to the bottom surface of the switch button frame.
Figure 21:
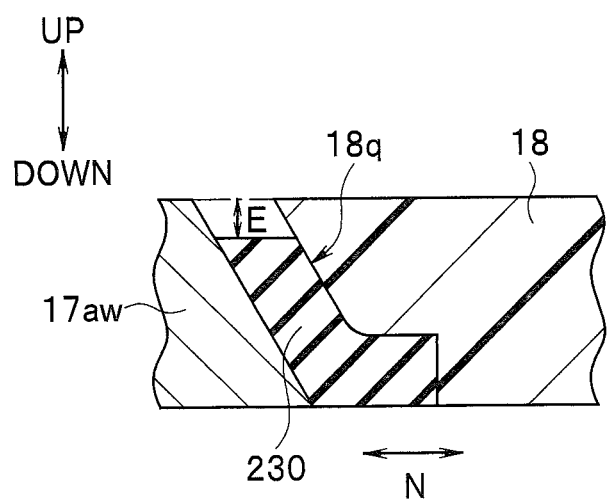
FIG. 21 is a partial cross-sectional view schematically showing a configuration of a modification in which the watertight member in FIG. 20 is so formed as to have an L-letter-like cross-sectional shape.

FIG. 18 is a partial cross-sectional view schematically showing a configuration in which an annular watertight member is provided on an outer circumferential surface of the switch button frame in FIG. 3 and further showing part of the main cover. FIG. 19 is a partial cross-sectional view schematically showing a configuration in which the watertight member in FIG. 18 is provided on a bottom surface of the switch button frame. FIG. 20 is a partial cross-sectional view schematically showing a configuration in which the watertight member in FIG. 19 is provided on an inclining surface that connects the outer circumferential surface to the bottom surface of the switch button frame. FIG. 21 is a partial cross-sectional view schematically showing a configuration of a modification in which the watertight member in FIG. 20 is so formed as to have an L-letter-like cross-sectional shape.

When the switch button frame 18 is attached and fixed to the opening section 90, and the watertight member 230 is formed on the outer circumferential surface of the switch button frame 18, as shown in FIG. 18, it is undesirably difficult to crush and press-fit the watertight member 230.

When the watertight member 230 is formed on the bottom surface of the switch button frame 18, as shown in FIG. 19, compressive reaction force produced by the watertight member 230 undesirably tends to warp the switch button frame 18.

To solve the problems described above, the watertight member 230 may be formed on an inclining surface 18*q*, which connects the outer circumferential surface and the bottom surface of the switch button frame 18, as shown in FIG. 20.

According to the configuration described above, in which the watertight member 230 also has a cross-sectional tapered shape, the resistance that occurs when the watertight member 230 is press-fit is reduced, and the watertight member 230 is readily crushed with the aid of a wedge effect based on the inclining surface 18*q* when the switch button frame 18 is pressed in the DOWN direction.

Therefore, since the watertight member 230 can be readily attached, and the watertightness can be ensured by the inclining surface 18*q*, a highly watertight member 230 can be provided.

The watertight member 230 may be so formed as to have an L-letter-like cross-sectional shape that extends from the inclining surface 18*q* toward the bottom surface of the watertight member 230, as shown in FIG. 21.

According to the configuration described above, when the switch button frame 18 is attached to the opening section 90, large tolerance E of precision of alignment between the wall section 17*aw* and the switch button frame 18 can be provided.

Figure 22:
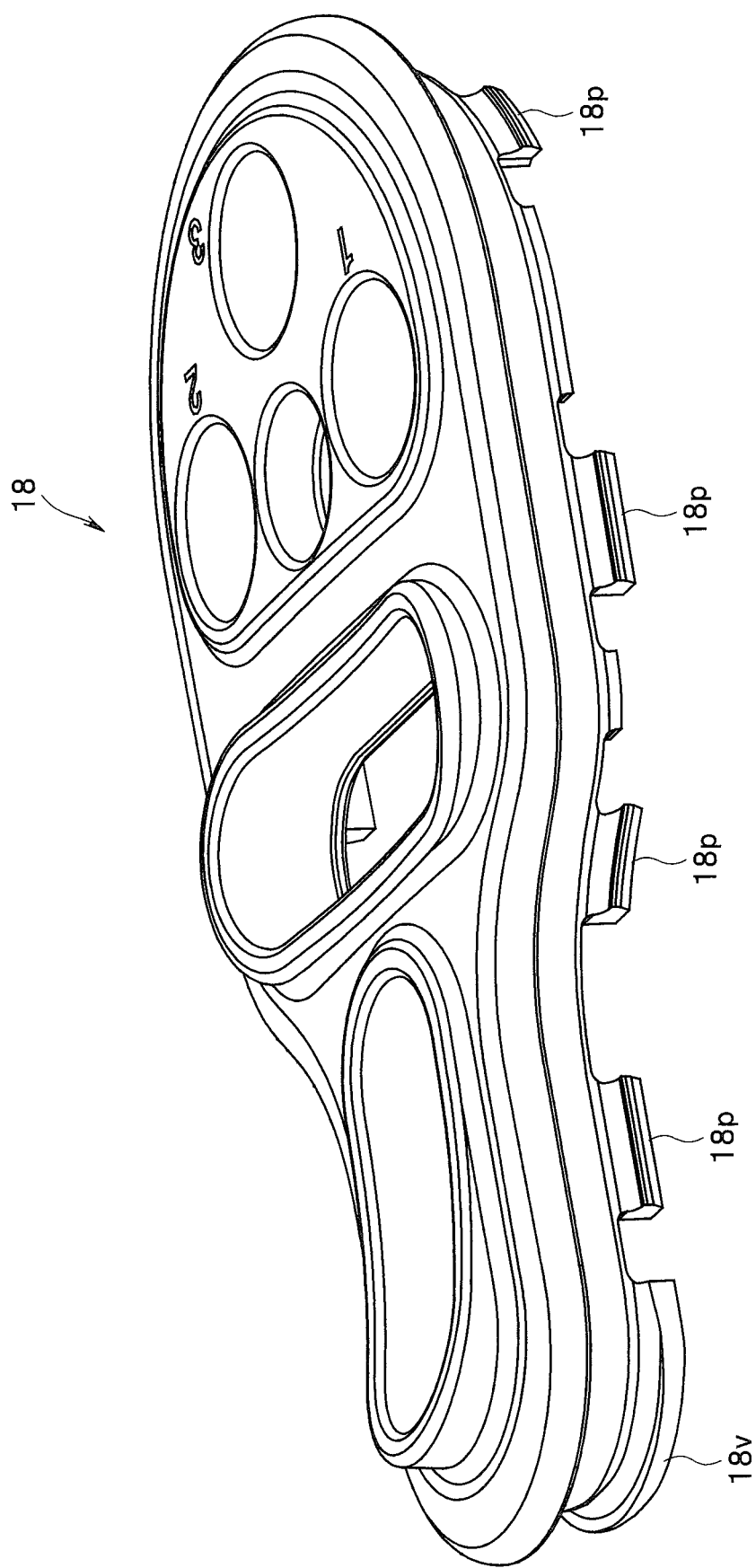
FIG. 22 is a perspective view showing a modification of the shape of the claw sections of the switch button frame in FIG. 3.

FIG. 22 is a perspective view showing a modification of the shape of the claw sections of the switch button frame in FIG. 3.

In the present embodiment described above, the switch button frame 18 is so configured that the plurality of elastically deformable claw sections 18*f* are caught in snap fitting by the catching protrusions 17*ad*.

Further, the switch button frame 18 is fixed to the outer surface 17*ag* of the upper portion of the main cover 17*a* with the single screw 19, so that the switch button frame 18 is watertightly fixed to the opening section 90.

Out of a plurality of claw sections 18*p*, the claw section 18*p* in a position farthest from the screw 19, for example, in a position of a distal end of the switch button frame 18 may be formed as a rigid claw section 18*v*, which has a large size in the outer circumferential direction of the switch button frame 18 and is not elastically deformed. The claw section 18*v* is only hooked to the corresponding catching protrusion 17*ad*.

According to the configuration described above, in which the claw section in the position farthest from the screw 19 is the rigid claw section 18*v*, the switch button frame 18 is fixed with improved strength also in the case where only the single screw 19 is used, as compared with the case where the claw sections are each elastically deformable. That is, resistance of the switch button frame 18 against external force is improved.

Further, using the rigid claw section 18*v* with a plurality of elastically deformable claw sections 18*p* allows a structure in which the switch button frame 18 is not readily detached after the switch button frame 18 is attached.

Figure 23:
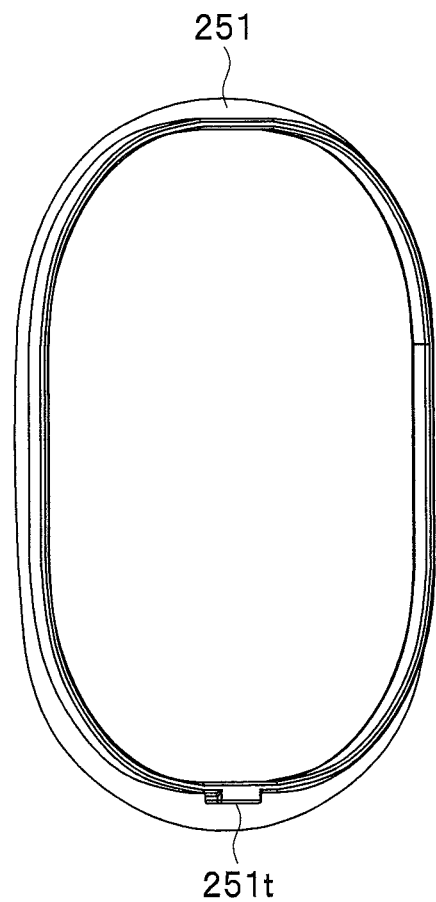
FIG. 23 is a perspective view showing the watertight member in FIG. 3 for a gold ring.
Figure 24:
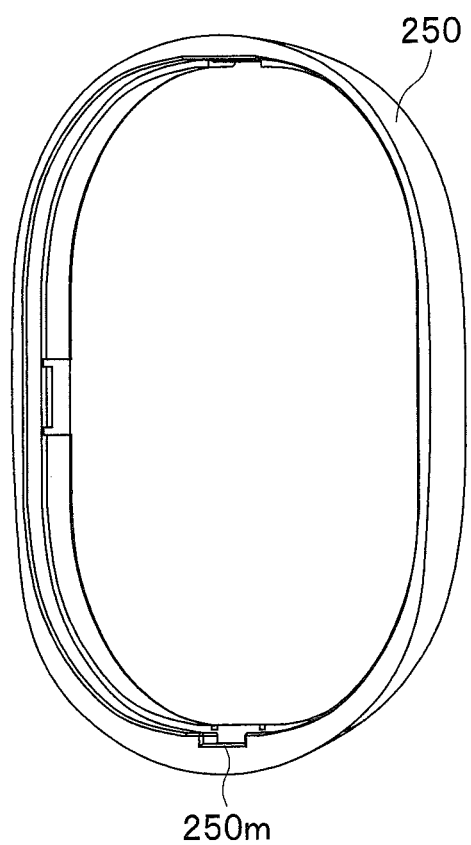
FIG. 24 is a perspective view showing the gold ring in FIG. 23.

FIG. 23 is a perspective view showing the watertight member for a gold ring in FIG. 3, and FIG. 24 is a perspective view showing the gold ring in FIG. 23.

An inner circumference of a distal end of the exterior cover 40 is watertightly fixed to an outer circumference of the distal end of the rear cover 17*b* via an annular watertight member 252, as shown in FIG. 3.

Further, on an outer circumference of the distal end of the exterior cover 40, a known gold ring 250, which is an index that allows the operator to visually recognize the function and other factors of the camera head, is provided in a position between the distal end of the exterior cover 40 and the proximal end of the main cover 17*a*.

To allow the gap between the gold ring 250 and the proximal end of the main cover 17*a* to be cleaned and disinfected in an improved manner, a configuration in which an annular watertight member 251 is further provided in the gap, as shown in FIG. 3, is also known.

However, in a case where an outer circumferential shape of the camera head 3 has a complicated streamline shape in consideration of the exterior appearance of the camera head 3, it is difficult to ensure the watertightness when the watertight member 251 is shifted in the direction of rotation. Further, part of the watertight member 251 undesirably extends off outward, and other problems occur.

In view of the problems described above, part of the watertight member 251 may be provided with a catching protrusion 251*t*, as shown in FIG. 23, and a catching groove 250*m*, which catches the catching protrusion 251*t*, may be formed in the gold ring 250.

According to the configuration described above, the configuration in which the catching protrusion 251*t* is caught by the catching groove 250*m* prevents the shift of the watertight member 251 from being shifted in the direction of rotation.

As a result, the watertightness of the watertight member 251 is sufficiently ensured, and the watertight member 251 will not extend off.

A configuration in which the gold ring 250 is provided with a catching protrusion and the watertight member 251 is provided with a catching groove can provide the same effect.

In the present embodiment described above, the switch unit 270 is used in the camera head 3, but not necessarily, and the switch unit 270 may, of course, be used in a standalone endoscope 2.

What is claimed is:

1. A switch unit comprising:
   an exterior member;
   a frame body fixed to the exterior member and in which a plurality of holes are formed, the frame body being provided separately from the exterior member;
   a plurality of switches provided in each of two of the plurality of holes;
   a soft switch cover that is disposed in each of the two holes and covers the plurality of switches;
   a switch fixing member that is disposed in each of the two holes and is covered with the switch cover to fix the plurality of switches to the exterior member;
   a first catch formed as part of the switch cover in a position between the plurality of switches in each of the holes, the first catch fixing the switch cover to the switch fixing member at the position; and
   a second catch formed at an outer circumference of the switch cover and caught by the frame body to fix the outer circumference of the switch cover to the switch fixing member.

2. The switch unit according to claim 1, wherein the frame body is arranged in a bottomed opening provided in a surface of the exterior member, the opening having a circumference covered with a wall.

3. The switch unit according to claim 2, wherein the first catch is a convex claw.

4. The switch unit according to claim 2, wherein the first catch is a concave groove that catches a convex claw provided as part of the switch fixing member.

5. The switch unit according to claim 2, wherein
   part of the switch cover is covered with the frame body, and
   a portion of the frame body that covers the switch cover is watertightly fixed to the opening via a watertight member.

6. The switch unit according to claim 2, wherein the exterior member in which the opening is formed is formed of one layer of metal.

7. An image pickup apparatus for endoscope comprising the switch unit according to claim 2.

8. An endoscope comprising the switch unit according to claim 2.

9. The switch unit according to claim 1, wherein the first catch comprises a projection and the switch fixing member is configured to catch the projection at the position to fix the switch cover to the switch fixing member at the position.

10. The switch unit according to claim 9, wherein the switch fixing member having a hole at the position, the hole being configured to catch the projection at the position to fix the switch cover to the switch fixing member at the position.

* * * * *